(12) United States Patent
Nitta

(10) Patent No.: US 6,557,551 B2
(45) Date of Patent: May 6, 2003

(54) UNIT FOR ADJUSTING HUMIDIFICATION

(75) Inventor: Kazufuku Nitta, Saitama-Ken (JP)

(73) Assignee: Respironics, Inc., Murrysville, PA (US)

( * ) Notice: Subject to any disclaimer, the term of this patent is extended or adjusted under 35 U.S.C. 154(b) by 0 days.

(21) Appl. No.: 10/138,878

(22) Filed: May 2, 2002

(65) Prior Publication Data

US 2002/0170559 A1 Nov. 21, 2002

Related U.S. Application Data

(62) Division of application No. 09/230,010, filed on Nov. 26, 1999, now Pat. No. 6,394,084.

(30) Foreign Application Priority Data

Jul. 16, 1996 (JP) .............................. 8-186364

(51) Int. Cl.[7] .............................................. A61H 16/00
(52) U.S. Cl. .......................... 128/203.17; 128/201.13; 128/204.17; 128/203.27; 128/204.18; 261/154; 261/DIG. 65
(58) Field of Search ....................... 128/201.13, 203.17, 128/203.26, 203.27, 204.17, 204.18, 204.21; 261/130, 154, DIG. 65, 104, 107

(56) References Cited

U.S. PATENT DOCUMENTS

| | | |
|---|---|---|
| 1,446,807 A | 2/1923 | Mercer |
| 3,414,863 A | 12/1968 | Lemelson |
| 3,501,619 A | 3/1970 | Buiting et al. |
| 3,507,627 A | 4/1970 | Frant et al. |
| 3,582,968 A | 6/1971 | Buiting et al. |
| 3,607,131 A | 9/1971 | Williams et al. |
| 3,616,796 A | 11/1971 | Jackson |
| 3,659,604 A | 5/1972 | Melville et al. |
| 3,688,083 A | 8/1972 | Rice et al. |
| 3,695,267 A | 10/1972 | Hirtz et al. |
| 3,707,966 A | 1/1973 | Nebel |
| 3,747,598 A | 7/1973 | Cowans |
| 3,834,682 A | 9/1974 | McPhee |
| 3,871,373 A | 3/1975 | Jackson |
| 3,916,891 A | 11/1975 | Freytag et al. |
| 3,934,117 A | 1/1976 | Schladitz |
| 3,948,316 A | 4/1976 | Souriau |
| 3,954,920 A | 5/1976 | Heath |

(List continued on next page.)

FOREIGN PATENT DOCUMENTS

| | | |
|---|---|---|
| EP | 0009543 | 4/1980 |
| EP | 0299381 | 1/1989 |
| EP | 0413127 | 2/1991 |
| FR | 2250542 | 6/1975 |
| FR | 2636845 | 3/1990 |
| GB | 2176405 | 12/1986 |
| JP | 3-125832 | 5/1991 |
| JP | 4-86437 | 3/1992 |
| JP | 7-301440 | 11/1995 |
| WO | WO 92/07601 | 5/1992 |

*Primary Examiner*—Aaron J. Lewis
*Assistant Examiner*—Mital Patel
(74) *Attorney, Agent, or Firm*—Michael W. Haas

(57) ABSTRACT

A humidification unit adapted to be disposed in a patient circuit for humidifying the flow of breathing gas delivered to the patient via the patient circuit by an artificial ventilator system. The humidification unit includes an exothermic member having an outer surface and a plurality of hollow fibers disposed on the outer surface of the exothermic member. Each hollow fiber is defined by a peripheral wall having minute openings large enough to allow a gas to pass therethrough yet small enough to prevent a liquid from passing therethrough. Liquid delivered to the hollow fibers is heated by the exothermic member and the gas vapor resulting from the heating passes through the hollow fiber walls and humidifies the flow of breathing gas delivered to the patient.

15 Claims, 13 Drawing Sheets

U.S. PATENT DOCUMENTS

| | | |
|---|---|---|
| 3,990,441 A | 11/1976 | Hoyt et al. |
| 4,010,748 A | 3/1977 | Dobritz |
| 4,014,382 A | 3/1977 | Heath |
| 4,028,445 A | 6/1977 | Hickmann et al. |
| 4,048,993 A | 9/1977 | Dobritz |
| 4,062,359 A | 12/1977 | Geaghan |
| 4,068,625 A | 1/1978 | Brown |
| 4,086,305 A | 4/1978 | Dobritz |
| 4,098,852 A | 7/1978 | Christen et al. |
| 4,110,419 A | 8/1978 | Miller |
| 4,146,597 A | 3/1979 | Eckstein et al. |
| 4,155,961 A | 5/1979 | Benthin |
| 4,187,390 A | 2/1980 | Gore |
| 4,190,046 A | 2/1980 | Virag |
| 4,195,044 A | 3/1980 | Miller |
| 4,201,204 A | 5/1980 | Rinne et al. |
| 4,225,542 A | 9/1980 | Wall et al. |
| 4,248,217 A | 2/1981 | Brisson |
| 4,300,925 A | 11/1981 | Nikandrov et al. |
| 4,303,601 A | 12/1981 | Grimm et al. |
| 4,305,388 A | 12/1981 | Brisson |
| 4,318,398 A | 3/1982 | Oetjen et al. |
| 4,327,717 A | 5/1982 | Oetjen et al. |
| 4,355,636 A | 10/1982 | Oetjen et al. |
| 4,367,734 A | 1/1983 | Benthin |
| 4,369,777 A | 1/1983 | Lwoff et al. |
| 4,381,267 A | 4/1983 | Jackson |
| 4,427,004 A | 1/1984 | Miller |
| 4,430,994 A | 2/1984 | Clawson et al. |
| 4,436,674 A | 3/1984 | McMenamin |
| 4,461,735 A | 7/1984 | Wirt |
| 4,477,395 A | 10/1984 | Albarda |
| 4,480,172 A | 10/1984 | Ciciliot et al. |
| 4,532,088 A | 7/1985 | Miller |
| 4,564,748 A | 1/1986 | Gupton |
| 4,621,632 A | 11/1986 | Bartels et al. |
| 4,621,633 A | 11/1986 | Bowles et al. |
| 4,629,590 A | 12/1986 | Bagwell |
| 4,652,408 A | 3/1987 | Montgomery |
| 4,657,713 A | 4/1987 | Miller |
| 4,674,494 A | 6/1987 | Wiencek |
| 4,676,237 A | 6/1987 | Wood et al. |
| 4,682,010 A | 7/1987 | Drapeau et al. |
| 4,704,988 A | 11/1987 | Mellet |
| 4,708,831 A | 11/1987 | Elsworth et al. |
| 4,753,758 A | 6/1988 | Miller |
| 4,770,168 A | 9/1988 | Rusz et al. |
| 4,771,770 A | 9/1988 | Artemenko et al. |
| 4,774,032 A | 9/1988 | Coates et al. |
| 4,822,533 A | 4/1989 | Steiner et al. |
| 4,825,863 A | 5/1989 | Dittmar et al. |
| 4,829,997 A | 5/1989 | Douwens et al. |
| 4,829,998 A | 5/1989 | Jackson |
| 4,861,523 A | 8/1989 | Beran |
| 4,910,384 A | 3/1990 | Silver |
| 4,921,642 A | 5/1990 | La Torraca |
| 4,943,704 A | 7/1990 | Rabenau et al. |
| 5,062,145 A | 10/1991 | Zwaan et al. |
| 5,109,471 A | 4/1992 | Lang |
| 5,148,801 A | 9/1992 | Douwens et al. |
| 5,163,423 A | 11/1992 | Suzuki |
| 5,172,686 A | 12/1992 | Anthony |
| 5,195,515 A | 3/1993 | Levine |
| 5,218,833 A | 6/1993 | Newbold |
| 5,226,411 A | 7/1993 | Levine |
| 5,255,674 A | 10/1993 | Oftedal et al. |
| 5,257,341 A | 10/1993 | Austin, Jr. et al. |
| 5,271,086 A | 12/1993 | Kamiyama et al. |
| 5,273,689 A | 12/1993 | Hamasaki |
| 5,318,731 A | 6/1994 | Yokoya et al. |
| 5,336,156 A | 8/1994 | Miller et al. |
| 5,348,691 A | 9/1994 | McElroy et al. |
| 5,349,946 A | 9/1994 | McComb |
| 5,357,948 A | 10/1994 | Eilentropp |
| 5,367,604 A | 11/1994 | Murray |
| 5,383,447 A | 1/1995 | Lang |
| 5,389,311 A | 2/1995 | Hetzel |
| 5,392,770 A | 2/1995 | Clawson et al. |
| 5,399,299 A | 3/1995 | Stengel et al. |
| 5,435,298 A | 7/1995 | Anthony |
| 5,462,048 A | 10/1995 | Lambert et al. |
| 5,537,996 A | 7/1996 | McPhee |
| 5,592,933 A | 1/1997 | Zucchi |
| 5,624,610 A | 4/1997 | Yokoya et al. |
| 5,640,951 A | 6/1997 | Huddart et al. |
| 5,647,344 A | 7/1997 | Turnbull |
| 5,653,920 A | 8/1997 | DiDomenico |
| 6,175,687 B1 | 1/2001 | Imamura et al. |

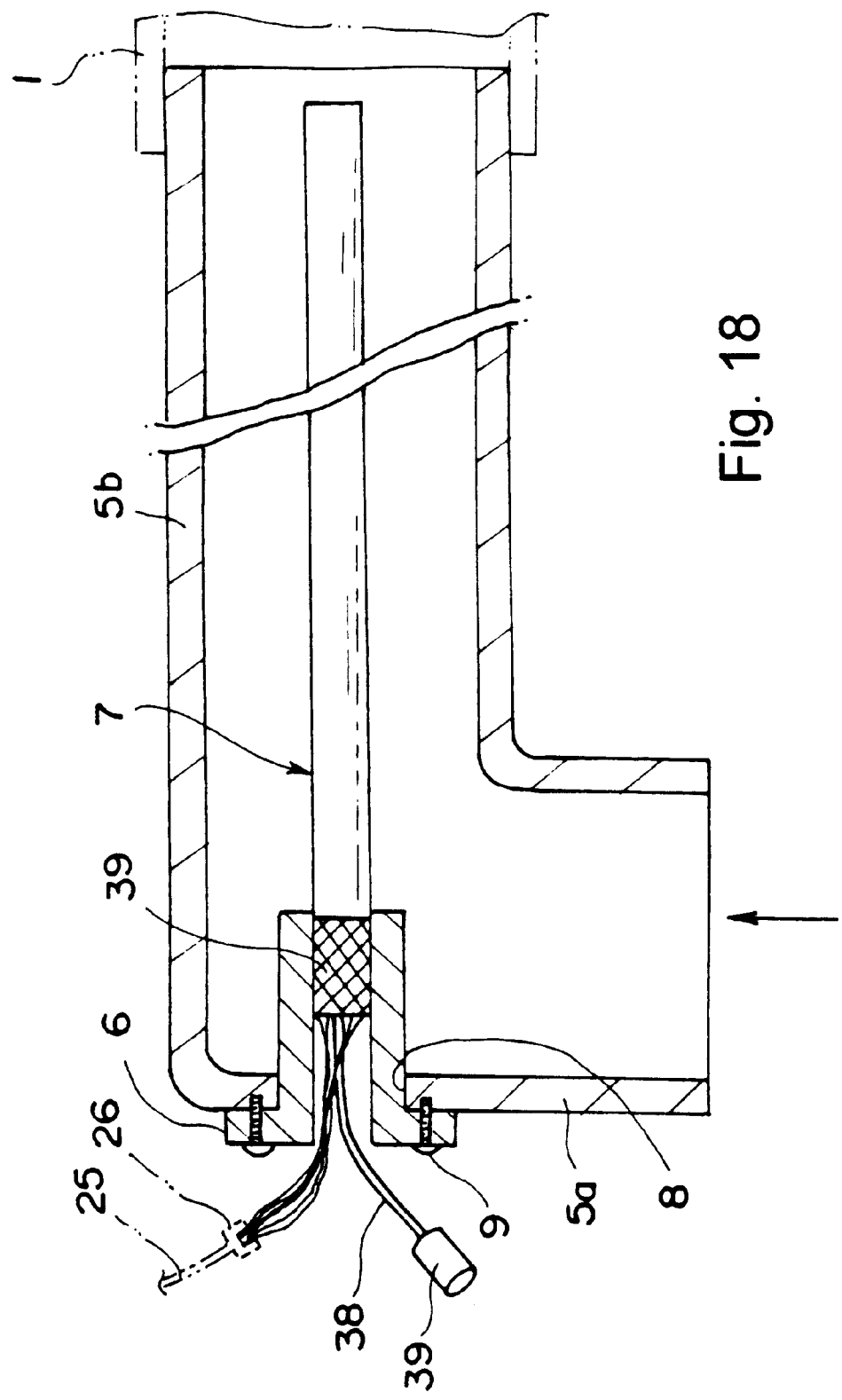

UNIT FOR ADJUSTING HUMIDIFICATION

This application is a divisional application of U.S. Ser. No. 09/230,010 filed Nov. 26, 1999 now U.S. Pat. No. 6,394,084.

BACKGROUND OF THE INVENTION

1. Field of the Invention

The present invention relates to a humidification unit, a humidifying unit for an artificial respiratory device, and a method for manufacturing of a humidification unit.

2. Description of the Related Art

Japanese Patent Application Unexamined Publication No. 62-26, 076 discloses a humidification unit that uses a gas permeable tube having a peripheral wall with minute openings defined in the wall. The openings are large enough to allow water vapor to permeate through the peripheral wall yet small enough to prevent water from passing therethrough. More specifically, this humidification unit includes a gas permeable tube having a peripheral wall with minute openings that are arranged in such a way that an electrically exothermic member having an inner diameter of at least 3 mm or larger is disposed in this single gas permeable tube. During use, the gas permeable tube communicates with a water supply source and is filled in with water. Water vapors are discharged from the gas permeable tube through the minute openings provided in the peripheral wall with the aid of heat generated from the electrically exothermic member.

The humidification unit described above, however, has a disadvantage in that should the gas permeable tube break, an unacceptably large amount of water is likely to leak outside the tube. For example, in the case where such a humidification unit is employed in a patient circuit for an artificial respiratory device, a large quantity of leaking water from the gas permeable tube may become hazardous, especially if the leaked water causes a decrease in the humidifying function or if the leaked water flows into the intake side of the artificial respiratory device, i.e., the side connected to a patient.

SUMMARY OF THE INVENTION

Accordingly, it is on object of the present invention to provide a humidification unit that does not suffer from the shortcomings of the above-described conventional humidification devices. It is a further object to provide a humidification unit that is capable of minimizing leakage from the humidification unit should the unit be damaged while still sustaining the humidifying function.

The present invention has a another object to provide an artificial respiratory system using such a humidification unit.

Further, the present invention has an object to provide a method for manufacturing such a humidification unit.

In order to achieve these objects, the present invention provides a humidification unit comprising an exothermic member having an outer surface and a plurality of hollow fibers disposed on the outer surface of the exothermic member. Each hollow fiber has a peripheral wall with minute openings that are large enough to allow a gas, such as water vapor, to permeate therethrough, yet small enough to prevent a liquid, such as water, from passing therethrough.

Furthermore, in order to achieve the above objects, the present invention provides a humidification unit comprising an exothermic member having an outer surface and a plurality of hollow fibers disposed on the outer surface of the exothermic member. Each hollow fiber has peripheral wall with minute openings that are large enough to allow a gas, such as water vapor, to permeate therethrough, yet small enough to prevent a liquid, such as water, from passing therethrough. The exothermic member and hollow fibers define a humidification element, which is coupled to a short connection tube that is adapted to be detachably connected to a patient circuit in an artificial respiratory system. Providing a support member in the form of the connection tube to which the humidification element is attached, allows the entire assemble to be readily disposed into the patient circuit.

In order to achieve the other objects as described herein above, the present invention provides an artificially respiratory system and method of using same that includes a pressure generator adapted to generate a flow of breathing gas, a patient circuit coupled to the pressure generator for delivering the flow of breathing gas to the patient, and a humidification unit disposed in the patient circuit. The humidification unit comprises an exothermic member having an outer surface and a plurality of hollow fibers disposed on the outer surface of the exothermic member. Each hollow fiber has peripheral wall with minute openings that are large enough to allow a gas, such as water vapor, to permeate therethrough, yet small enough to prevent a liquid, such as water, from passing therethrough. In a further embodiment, a fluid supply source communicates with the multiple hollow fibers to supply liquid thereto.

The above objects are also achieved by providing a method for preparing a humidification unit that includes the steps of providing a plurality of hollow fibers, wherein each hollow fiber is defined by a peripheral wall having minute openings large enough to allow a gas to pass therethrough, yet small enough to prevent a liquid from passing therethrough, and winding the hollow fibers around an exothermic member such that the plurality of hollow fibers are disposed on the outer surface of the exothermic member. In a further embodiment, the plurality of hollow fibers are arranged in a sheet, and the sheet of hollow fibers are wound around the exothermic member such that a longitudinal axis of the plurality of hollow fibers is substantially parallel to a longitudinal axis of the exothermic member. In a still further embodiment, the plurality of hollow fibers are arranged in a strip, and the strip of hollow fibers are wound around the exothermic member in spiral fashion.

Because the plurality of hollow fibers disposed on the outer surface of the exothermic member define a humidification element with a relatively small diameter and because each hollow fiber has a peripheral wall with minute openings that are large enough to allow a gas to permeate therethrough, yet small enough to prevent a liquid from passing therethrough, the humidification element can be disposed in a path having a small diameter, and can still provide a significant humidifying function by heating the multiple hollow fibers with the exothermic member. Furthermore, even if a few of the hollow fibers are damaged, broken, etc., the humidifying function is not significantly compromised, and water leaking from the humidification element is minimized. In addition, the exothermic member supports the multiple hollow fibers so that the entire unit can be transported and handled relatively easily.

By providing an exothermic member that consists of an electrically controlled exothermic member, the amount of heat to be applied to the water in the multiple hollow fibers can be controlled, without waste and with a high degree of precision. Accordingly, the humidification unit according to the present invention can ensure reliability and stability in its humidifying function.

By providing an exothermic member consisting of a heating wire for generating heat upon transmission of electric current thereto, and by providing an electrically insulating member disposed around the heating wire for ensuring electrical insulation, the humidification unit can ensure safety upon use, because the insulating performance can be ensured even if an electrically powered exothermic member is employed as the exothermic member.

On the other hand, by providing a heat pipe as the exothermic member, the structure of the humidification unit can be simplified, because it does not require electrical insulation. Such a heat pipe also provides support for the multiple hollow fibers held on the heat pipe employed as the exothermic member.

Winding the multiple hollow fibers around the exothermic member improves the transmission of heat from the exothermic member to the multiple hollow fibers. In addition, the humidifying ability can be readily increased or decreased by adjusting the amount of the multiple hollow fibers wound around the exothermic member.

In a further embodiment of the present invention, the ends the multiple hollow fibers are joined together and a connector is provided for connecting the fibers to a fluid source. In a still further embodiment, the connector to the supply of fluid is located on only one end of the fibers, thereby simplifying the use of the humidification unit so that only one fluid connection is required. In another embodiment, however, both ends of the multiple hollow fibers are connected to the fluid supply source to allow fluid to be supplied to both ends of the multiple hollow fibers so that the supply of fluid to each of the multiple hollow fibers can be performed at a high speed and with high precision. Also, should one supply of fluid fail or become blocked, the other serves as a backup.

If the multiple hollow fibers are joined at one end portion, which is the same as the side of the electric current supply end of the exothermic member, the electric current supply system and the water supply system can be concentrated at one location.

These and other objects, features and characteristics of the present invention, as well as the methods of operation and functions of the related elements of structure and the combination of parts and economies of manufacture, will become more apparent upon consideration of the following description and the appended claims with reference to the accompanying drawings, all of which form a part of this specification, wherein like reference numerals designate corresponding parts in the various figures. It is to be expressly understood, however, that the drawings are for the purpose of illustration and description only and are not intended as a definition of the limits of the invention.

BRIEF DESCRIPTION OF THE DRAWINGS

FIG. 18 is a perspective view showing the humidifying element according to a tenth embodiment of the present invention.

DETAILED DESCRIPTION OF THE PRESENTLY PREFERRED EMBODIMENTS OF THE INVENTION

Figure 1:
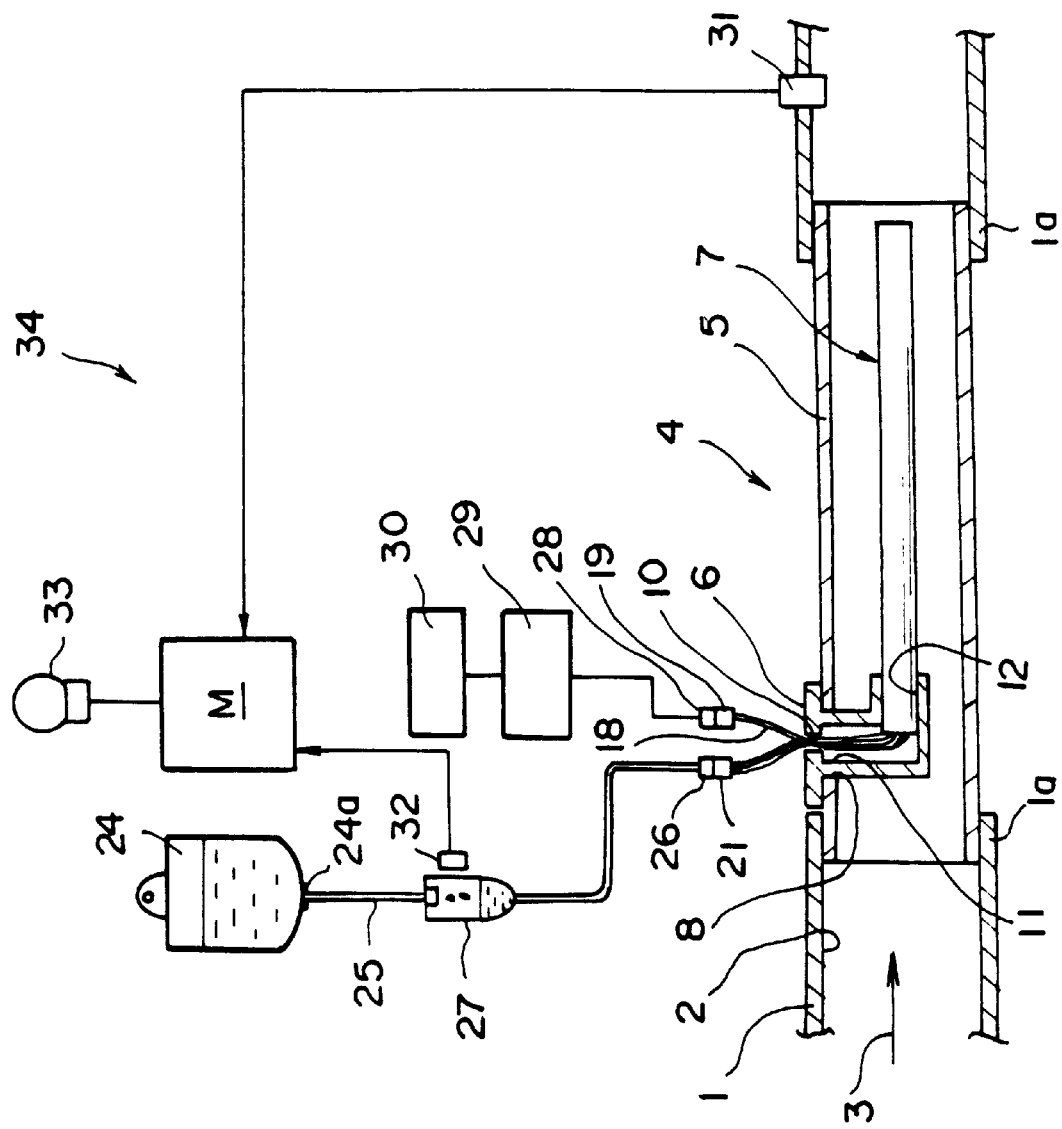
FIG. 1 is a structural diagram showing a humidifying unit for an artificial respiratory device according to a first embodiment of the present invention.

The present invention will be described by way of examples with reference to the accompanying drawings. FIGS. 1 to 7 show the humidification unit according to a first embodiment of the present invention. As shown in FIG. 1, reference numeral 1 denotes a patient circuit in an artificial respiratory device suitable for connecting an adapter (not shown), which is connected to the lungs of a patient, to a source of breathing gas. An inner portion of patient circuit 1 constitutes an intake path 2 for the delivery of breathing gases to an airway of the patient from a supply of breathing gas, such as a pressure generator. The flow of breathing gas in patient circuit 1 is indicated by arrow 3. The inner diameter of patient circuit 1 may be set to be in the range of, for example, from 14 mm to 16 mm for an infant patient and from 20 mm to 24 mm for an adult patient.

Figure 2:
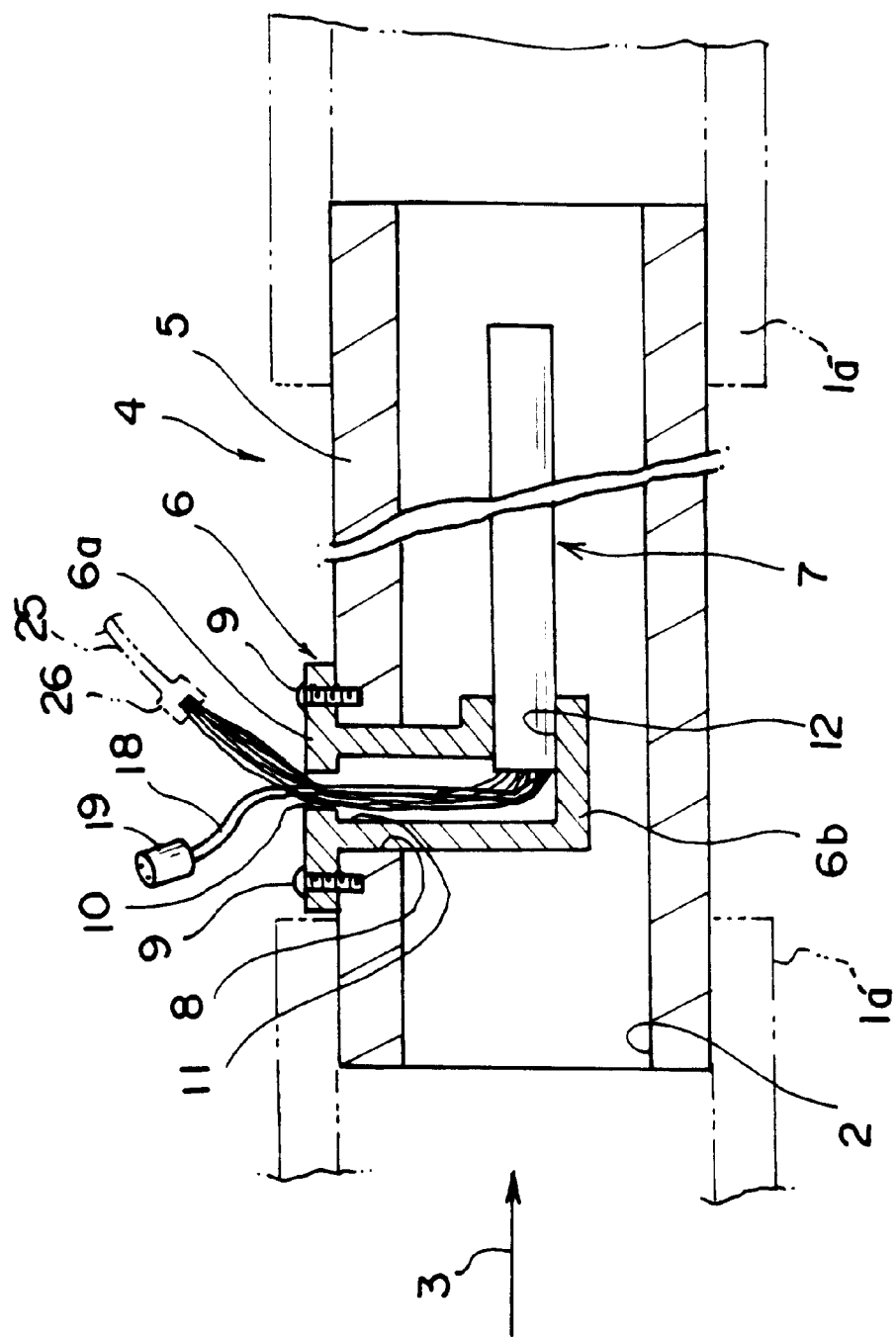
FIG. 2 is a diagram showing an enlarged portion of the humidifying unit of FIG. 1.

In the embodiment shown in FIGS. 1 and 2, patient circuit 1 is mounted detachably to a humidification unit 4 that is provided with a short connection tube 5 as a support member, a mounting flange 6, and a humidifying element 7. Connection tube 5 may be a straight tube with both end portions engaged (connected) in an airtight fashion to connection end portions 1a of patient circuit 1. The outer diameter of connection tube is set so as to be somewhat larger than the inner diameter of patient circuit 1, in order to ensure the airtight engagement with patient circuit to be connected thereto, and it may be set appropriately in accordance with the patient circuit to be employed. As a matter of course, in this case, the relationship of engagement of connection tube 5 with connection end portions 1a of patient circuit 1 may be such that the inner periphery of connection tube 5 is engaged with the outer periphery of connection end portions 1a of patient circuit 1. In such a case, the inner diameter of connection tube 5 is set to be somewhat smaller than the outer diameter of connection end portions 1a of patient circuit 1 to be connected thereto, in order to ensure the airtight engagement with patient circuit 1 to be connected thereto. Further, in this case, the use of a packing, a fastening band or the like may be employed in order to enhance airtightness.

The peripheral wall on one end of connection tube 5 (e.g., on the left side in FIGS. 1 and 2) is formed with a mounting opening 8 for mounting flange 6. Mounting opening 8 is located at a position outside of connection end portion 1a of patient circuit 1 upon connection with connection end portion 1a and disposed so as to allow the inside of connection tube 5 to communicate with the outside thereof.

In the illustrated exemplary embodiment, mounting flange 6 consists of a flange portion 6a in a square-plate shape or the like and a cylindrical holding portion 6b. Flange portion 6a of mounting flange 6 is shaped so as to be disposed along an outer peripheral wall of connection tube 5 and it is fixed to connection tube 5 by a screw 9 so as to cover the mounting opening 8 of connection tube 5 in a tight manner. Flange portion 6a is further provided with a communicating opening 10 that allows mounting opening 8 of connection tube 5 to open to the outside in the center of flange portion 6a.

Holding portion 6b of mounting flange 6 is disposed so as to stand upright with respect to the plate surface of flange portion 6a, such that opening 10 of flange portion 6a faces an opening 11 at the base end thereof. Holding portion 6b is arranged so as to insert through mounting opening 8 of connection tube 5 over the entire length of mounting opening 8 of connection tube 5, extending up to the center of connection tube 5 in the radial direction, and then curved on the other end side of connection tube 5 at a generally right angle (on the right end side in FIGS. 1 and 2). An opening 12 is defined in holding portion 6b so as to face an open end of connection tube 5. Opening 12 at one end of holding portion 6b is large enough to engage and hold humidifying element 7, and opening 12 is arranged so as to communicate to the outside through communicating opening 10 of flange portion 6a in holding portion 6b.

Figure 3:
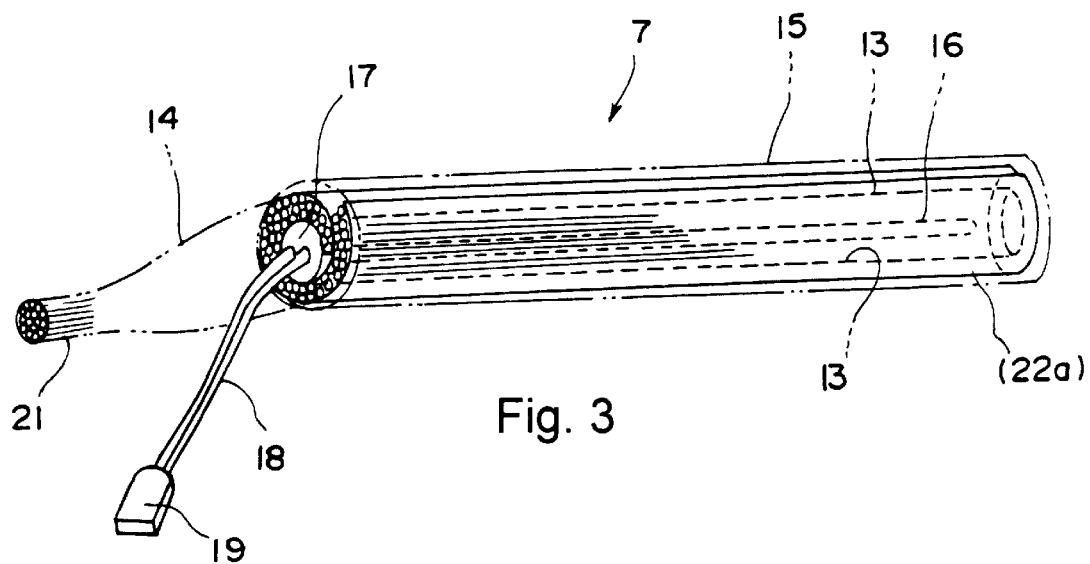
FIG. 3 is a perspective view showing a humidifying element employed in the humidifying unit of FIG. 1.

As shown in FIG. 3, humidifying element 7 comprises exothermic member 13, multiple hollow fibers 14 held at the outer surface of exothermic member 13, and a mesh cover tube 15 covering exothermic member 13 and multiple hollow fibers 14. In this embodiment of the present invention, exothermic member 13 is an electrically powered exothermic member of a columnar shape and has a diameter in the range of, for example, from approximately 3 mm to 6 mm, and an entire length in the range of, for example, from approximately 1 m to 2 m. The length in left-hand and right-hand directions in FIGS. 1 and 2) of exothermic member 13 is shorter that the axial length of connection tube 5. Exothermic member 13 comprises a heating wire 16 (a heater wire) and an electrically insulating member 17 enclosing the periphery of heating wire 16. Heating wire 16 is disposed in the inside of electrically insulating member 17 and has the function of generating heat upon receiving an electric current. A connection cord 18 is connected to heating wire 16 and extends from one end of exothermic member 13. An end portion of connection cord 18 is provided with a connector 19 for supplying electric current to the heating wire.

Each hollow fiber constituting the multiple hollow fibers 14 has a peripheral wall with minute openings (for example, a porosity rate of approximately 57.8%) which allows a gas, such as water vapor, to permeate therethrough, yet prevents a liquid, such as water, from passing therethrough. Each hollow fiber is minute in size (for example, having an outer diameter of 413 microns, an inner diameter of 282 microns, and an entire length of approximately 1.2 meters–1.5 meters). In one embodiment of the present invention, the multiple hollow fibers (the total number of from 40 to 60 hollow fibers in this embodiment) are disposed such that the axis of each hollow fiber 14 is nearly parallel to the longitudinal axis of exothermic member 13 and the entire periphery of exothermic member 13 is covered with multiple hollow fibers 14. In this embodiment, multiple hollow fibers 14 are folded not rolled in the direction in which they extend, and exothermic member 13 is covered with the folded multiple hollow fibers. The end portions of multiple hollow fibers 14 is arranged so as to extend outward from the ends of the exothermic member 13.

Figure 4:
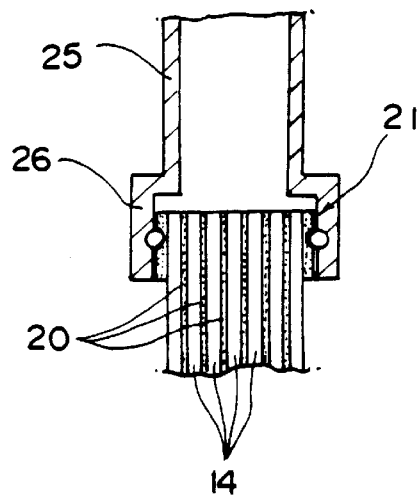
FIG. 4 is a cross-sectional view of a connector for the humidifying unit of FIG. 1.

As shown in FIGS. 3 and 4, the end portions of multiple hollow fibers 14 are joined together at a position outside of either end of exothermic member 13 via an adhesive agent 20 into a bundled state. The bundled portion is formed with a connector 21 having a given shape for supplying water to the hollow fibers. Upon forming connector 21, adhesive agent 20 may penetrate into the inside of the multiple hollow fibers 14 so that the end portion of the bundled multiple hollow fibers 14 into which the adhesive agent has penetrated can be cut in round slices to form a new end surface. Connection cord 18 is disposed so as to extend through multiple hollow fibers 14.

As shown in FIG. 3, mesh cover tube 15 is in a mesh that extends in both its axial and radial directions. Mesh cover tube 5 has an opening extending axially over the entire length and communicating the inside to the outside thereof. Exothermic member 13 and multiple hollow fibers 14 wound around the outer surface of exothermic member 13 are inserted into mesh cover tube 15 in a tight fashion. Multiple hollow fibers 14 are allowed to press against the outer surface of exothermic member 13 by an appropriate degree of pressing force that is created by the force due to the contraction of mesh cover tube 13.

Humidifying element 7 mainly has an extended shape depending upon the shape of exothermic member 13 and it is shaped such that the diameter of the humidifying element is smaller than the inner diameter of connection tube 5 and such that the length is shorter than the axial length of connection tube 5. Humidifying element 7 is arranged so as to be accommodated in its entirety within connection tube 5.

The end portion (the left end portion in FIGS. 1 and 2) of humidifying element 7 is held in a tight engagement with the end portion of holding portion 6b of mounting flange 6 in connection tube 5. On the other hand, the other end portion (the right end portion in FIGS. 1 and 2) of humidifying element 7 is a free end and extends toward the other end of connection tube 5. Further, the connection cord 18 and multiple hollow fibers 14 extend from holding portion 6b toward the outside of mounting flange 6 through communicating opening 10. Connector 21 and connector 19 are located outside of mounting flange 6.

Figure 5:
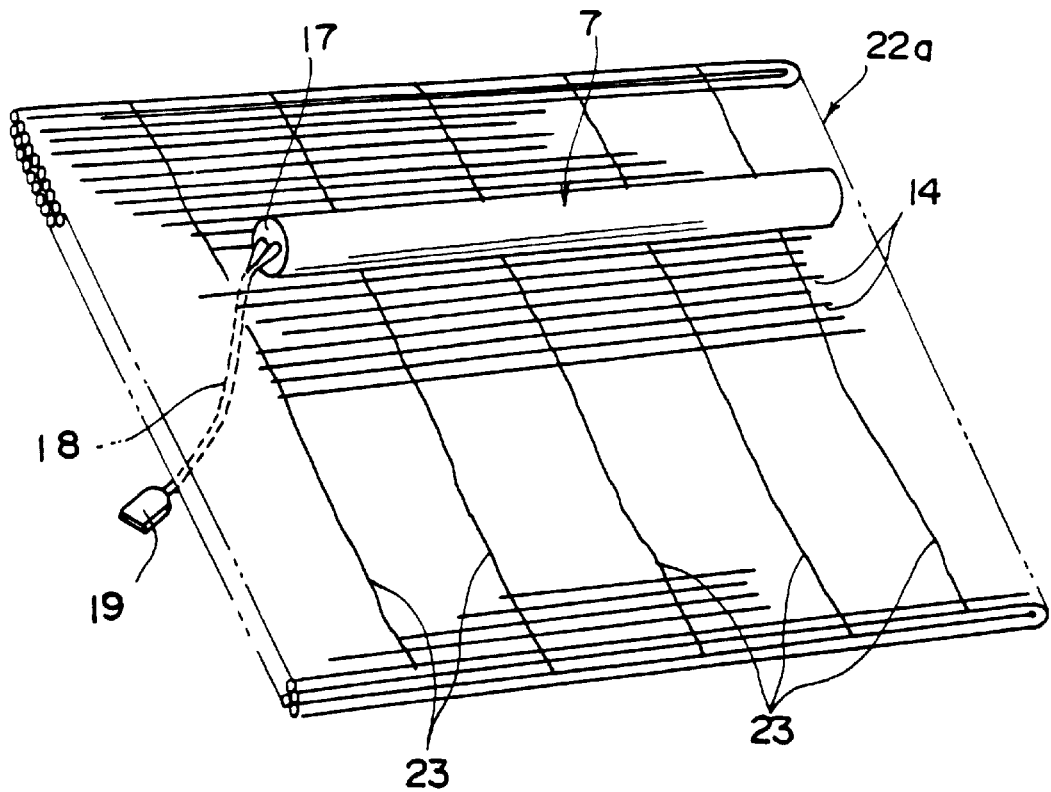
FIG. 5 is a perspective view illustrating a step in the preparation of the humidifying unit of FIG. 1.
Figure 6:
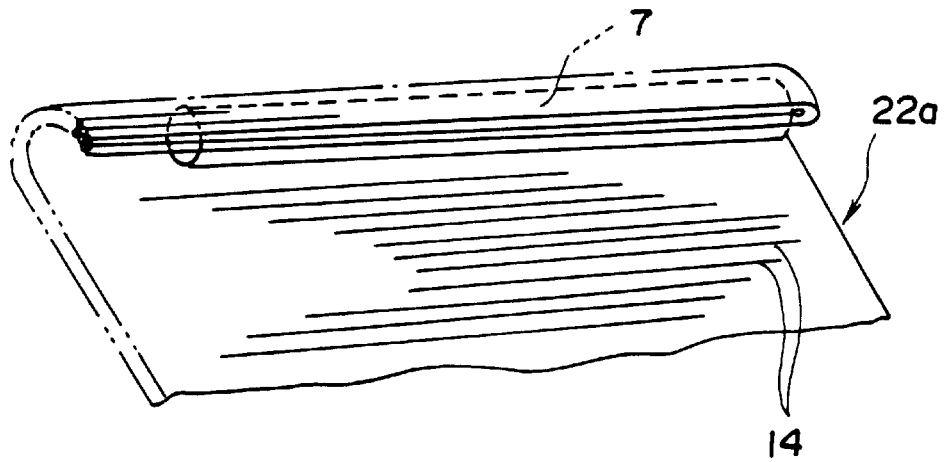
FIG. 6 is a perspective view illustrating a further step in the preparation of the humidifying unit of FIG. 1.
Figure 7:
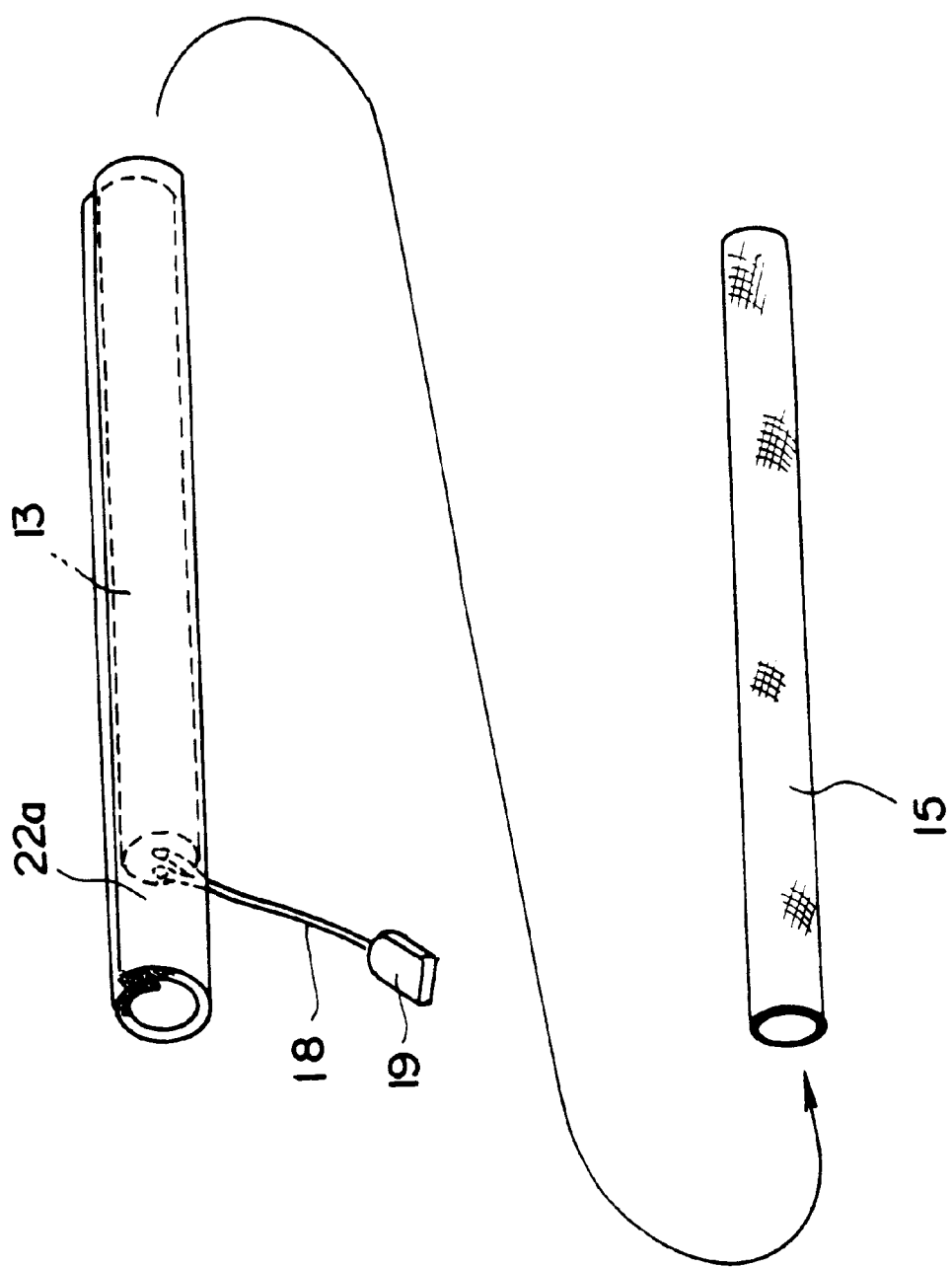
FIG. 7 is a perspective view illustrating a still further step in the preparation of the humidifying unit of FIG. 1.

Humidifying element 7 may be prepared in the steps as shown in FIGS. 5 to 7. As shown in FIG. 5, first, multiple hollow fibers 14, each having the peripheral wall with minute openings that are large enough to allow water vapor to permeate therethrough, yet small enough to prevent water from passing therethrough, are prepared so as to be formed into a sheet in which the axis of the multiple hollow fibers 14 are arranged so as to be generally parallel to each other. By combining the multiple hollow fibers in the manner as described herein above, the multiple hollow fibers can be treated in a collective manner, thereby making it relatively easy to attach the multiple hollow fibers to exothermic member 13. In this case, a string member 23 or the like may be employed to join multiple hollow fibers 14 integrally to each other into the sheet of multiple hollow fibers.

Then, as shown in FIG. 5, multiple hollow fiber sheet 22a is folded in the lengthwise direction in which each of the multiple hollow fibers 14 extends, and exothermic member 13 is disposed within folded multiple hollow fiber sheet 22a. At this time, the other end portion of exothermic member 13 is arranged so as to be even with the folded portion of multiple hollow fiber sheet 22a, while attention is being paid to the fact that the folded portion of multiple hollow fiber sheet 22a is not squashed and that the axis of exothermic member 13 is arranged so as to be generally parallel to the axis of multiple hollow fibers 14. Further, both end portions of multiple hollow fibers 14 are disposed so as to project outward from the one end portion of exothermic member 13.

Thereafter, as shown in FIG. 6, folded multiple hollow fiber sheet 22a is wound around exothermic member 13. By holding multiple hollow fibers 14 to the outer surface of exothermic member 13 and arranging multiple hollow fibers 14 so as to increase the area of exothermic member 13 in which multiple hollow fibers 14 are held to exothermic member 13, the humidifying ability of humidifying element 7 (the humidification unit 4) is improved.

At this time, as shown in FIGS. 5 and 7, connection cord 18 is disposed so as to extend through multiple hollow fibers 14 and project toward the outside of wound multiple hollow fiber sheet 22a. This allows the work for forming connector 21 to be conducted with relative east in the step that follows.

Then, as shown in FIG. 7, multiple hollow fiber sheet 22a and exothermic member 13 are inserted tightly into extendable mesh cover tube 15. The multiple hollow fibers are held with high precision to exothermic member 13 and each of the multiple hollow fibers is in contact with exothermic member 13 with an appropriate degree of the pressing force, thereby improving the transmission of heat from exothermic member 13 to multiple hollow fibers 14.

Next, as shown in FIGS. 3 and 4, the end portion of the folded hollow fiber sheet 22a is joined together with adhesive agent 20 into a bundle. The bundled portion is formed with connector 21 to form humidifying element 7. This does not require a connector to be prepared separately and, therefore, reduces the number of parts. Further, this configuration allows water to be supplied to multiple hollow fibers 14 from both ends of the multiple hollow fibers 14, for example, thereby allowing each of multiple hollow fibers 14 to be filled with water at a high speed and with a high degree of precision.

Connector 21 may be formed by combining the end portions of multiple hollow fibers 14 together or by separately combining each of the end portions of multiple hollow fibers 14 together.

As shown in FIG. 1, connector 21 of humidifying element 7 prepared in the manner as described herein above, is connected through a water supply tube 25 to a water bag 24 as a source of supplying water to the hollow fibers. Water bag 24 is filled with a predetermined amount of water, and the amount of water in the water bag 24 can be visually confirmed, because water bag 24 is made of a transparent or translucent material. Water bag 24 is mounted on a pole (not shown). Water bag 24 is further provided with a water outlet 24a at its lower portion and with an opening (not shown) at its upper portion through which the inside of the bag communicates to the outside.

Water supply tube 25 has one end portion connected (for example, held by engagement) to water outlet 24a of water bag 24 and another end portion formed with a connector 26 (schematically shown) as the counterpart of connector 21, as shown in FIGS. 1 and 4. Connector 26 is formed so as to engage connector 21 in an airtight manner by a one-touch operation.

Further, as shown in FIG. 1, water supply tube 25 is provided with a water drop counting device 27 as a flow meter for measuring the flow of water therethrough. The water drop counting device 27 is arranged so as to allow a flow of water to multiple hollow fibers 14 after the water has been dropped from water bag 24 into the water drop counting device 27. Further, water drop counting device 27 is arranged so as to visually confirm the state in which the water drops.

Connected to connector 19, as shown in FIG. 1, is another connector 28 for supplying of electric current to exothermic number 13. The other end of electric connector 28 is connected to a power source 30 through an adjustment unit 29. By connecting connectors 19 and 28, electric current is allowed to be supplied to heating wire 16, thereby generating heat and warming each of the multiple hollow fibers 14 to cause them to discharge water vapor into the flow of breathing gas 3 from multiple hollow fibers 14. The amount of the water vapor discharged may be adjusted automatically on the basis of the difference between the pressure of the water vapor in multiple hollow fibers 14 and the pressure of the water vapor in patient circuit 1.

It can be appreciated that the temperature of the flow of breathing gas can be controlled by the exothermic member 13 so as to remain below a predetermined temperature, that is, a temperature at which inconveniences may be caused to occur for the patient.

In FIG. 1, reference symbol M denotes a monitor. In the illustrated embodiment, monitor M is supplied on the downstream side of humidification unit 4 with signals from a temperature-moisture sensor 31 for sensing the temperature and the moisture of the flow of breathing gas and signals from a water drop detecting sensor 32 for sensing water drops in the water dropping device 27. Monitor M monitors these signals and operates an alarm (for example, an alarm lamp or an alarm buzzer) if the monitored characteristic becomes higher than a set level.

Therefore, humidifying system 34, with the structure as described herein above, as a matter of course, humidifies the flow of breathing gas to an appropriate extent by discharging water vapors from humidifying element 7 when humidifying element 7 is disposed in patient circuit 1. Further, humidifying system 34 is adapted so as to monitor the breakage of hollow fibers 14 or other damages (i.e., a leakage of water from hollow fibers 14) with extremely high precision, because the water drop detecting sensor can sense the leakage of water, even if very small, from hollow fibers 14 due to the breakage or damage of the hollow fibers as a variation in the flow of water drops through water dropping unit 27 (i.e., whether the set flow rate is satisfied), and the detected flow is transmitted to monitor M and then to alarm 33.

Furthermore, in this embodiment of the present invention, in addition to the contents as described herein above, multiple hollow fibers 14 are each extremely small in diameter. Therefore, even if hollow fibers 14 are broken or damaged or undergo other faults, the amount of water leaking from hollow fibers 14 can be minimized to an extremely small level, so that the humidifying ability of the humidifying unit according to the present invention is not significantly reduced and the inconveniences and problems which may otherwise be caused due to the leakage of water are also minimized.

In this case, although multiple hollow fibers 14 are generally flexible, they are held on exothermic member 13 that is physically stronger, so that exothermic member 13 provides function of supporting flexible hollow fibers 14. Therefore, multiple hollow fibers 14 can always sustain their predetermined shape without requiring a separate supporting means by taking advantage of exothermic member 13 as a unit for holding the shape of multiple hollow fibers 14.

Further, exothermic member 13 has a columnar shape extending in both directions so that the area of the exothermic member for heating the multiple hollow fibers and the area thereof for holding them can be increased rapidly, thereby enabling improvements in the humidifying ability and enhancing the ability of holding the shape of multiple hollow fibers 14.

Furthermore, as exothermic member 13 consists of electrically powered exothermic member, the amount of heating of multiple hollow fibers 14 (i.e., the water contained herein) can be controlled without waste and with high precision, thereby providing reliability and safety for the humidifying ability of the humidification unit 4 according to the present invention.

In this case, there is provided electrically insulating member 17 enclosing the heating wire 16 for ensuring electrical insulation. Thus, even if an electrically powered exothermic member is employed as exothermic member 13, safety during use can be ensured.

Furthermore, multiple hollow fibers 14 are wound around exothermic member 13 in such a manner that the axis of each of hollow fiber is arranged so as to be generally parallel to the axis of exothermic member 13, thereby ensuring a secure contact of each hollow fiber with the outer surface of exothermic member 13, thereby improving the transmission of heat to each hollow fiber from exothermic member 13. In addition, the amount of multiple hollow fibers 14 wound around exothermic member 13 can be readily adjusted, thereby allowing a ready increase or a decrease of the humidifying ability of the humidification unit according to the present invention.

In addition, multiple hollow fibers 14 are bundled (joined) outside one end of the exothermic member 13 and formed with connector 21 for connection to water bag 24. Therefore, the humidification unit according to the present invention minimizes the number of parts, because such a connector is not required to be prepared separately.

Further, connector 21 for supplying water is located on one end of exothermic member 13. By using one end of exothermic member 13 as the side for supporting a mounting object, the supporting system, the water supply system, and the electric current supply system of the humidification unit 4 according to the present invention can be concentrated at one location, thereby simplifying the manner of use and the structure of connection and making the connection more efficient.

On the other hand, each of the multiple hollow fibers can also be filled with water at a high speed and with high precision by supplying water to the multiple hollow fibers 14 from both ends. As the peripheral wall of each of the multiple hollow fibers 14 is provided with minute openings that are each large enough to allow water vapor to permeate therethrough, yet small enough to fail to permeate water therethrough, air present in each of the multiple hollow fibers 14 can be discharged through the minute openings formed in the peripheral walls of the multiple hollow fibers as the water is supplied thereto. Hence, each of the multiple hollow fibers 14 can always be filled in with water without the presence of air therein.

Furthermore, even if one end of the multiple hollow fibers should be blocked, water can still be supplied to the multiple hollow fibers 14 form the other end. This arrangement, therefore, enhances the reliability of the water supply to each of the multiple hollow fibers.

Further, in this embodiment of the present invention, humidification unit 4 is provided with connection tube 5 having a straight tube shape so that it can be readily set in place in patient circuit 1 simply by connecting connection tube 5 to connection end portion la of patient circuit 1. This improves ease of setting the humidification unit in place.

In addition, because humidifying element 7 is combined in a unit, the assembly of the humidifying element with connection tube 5 can be performed in a simplified manner using mounting flange 6. Further, the humidifying element can be assembled directly with patient circuit 1 in a simplified manner by forming the mounting opening 8 in the patient circuit 1.

Further, as humidifying element 7 is accommodated in connection tube 5 in its entirety, the humidifying element is protected by the connection tube, whereby the mounting operation, the transferring operation and other operations can be carried out in a convenient manner.

In addition, as exothermic member 13 and multiple hollow fibers 14 are inserted into extendable mesh cover tube 15 in a tightly engaged manner, the multiple hollow fibers can be held around the exothermic member with high precision and the transmission of heat from the exothermic member to each of the multiple hollow fibers can be improved, by allowing each of the multiple hollow fibers to come into contact with the exothermic member with an appropriate degree of pressing force.

Figure 8:
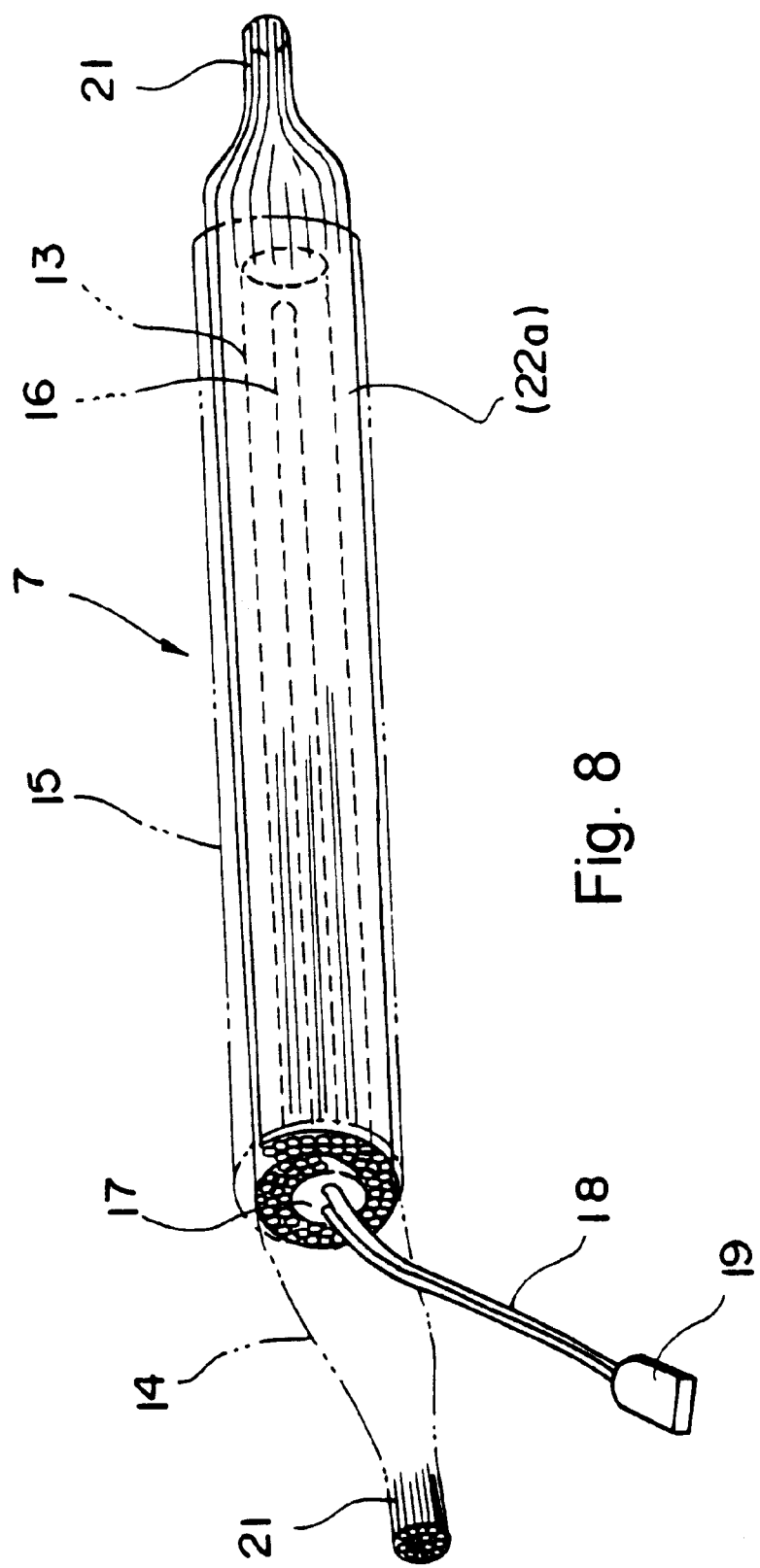
FIG. 8 is a perspective view showing a humidifying element according to a second embodiment of the present invention.

FIG. 8 et seq, show other embodiments of the humidification unit according to the present invention. In each of the embodiments that follow, the same structuring elements as in the first embodiment are provided with the identical reference numerals and symbols and a duplicate description will be omitted.

FIG. 8 shows the humidification unit according to a second embodiment of the present invention. In the second embodiment, multiple hollow fibers 14 are bundled (joined) at both ends of the exothermic member 13 and the bundled portions are formed each with connector 21 to be connected to water bag 24.

The humidification unit according to this embodiment can reduce the number of parts because a connector is not required to be prepared separately. Further, water can be filled in each of the multiple hollow fibers at a high speed and with high precision, because the water is supplied to each of the multiple hollow fibers from both ends thereof. In addition, even if multiple hollow fibers 14 would be blocked at the connector on either side of exothermic member 13, water can still be supplied to each of the multiple hollow fibers from the other connector, thereby enhancing the reliability in supplying water to each of the multiple hollow fibers.

Figure 9:
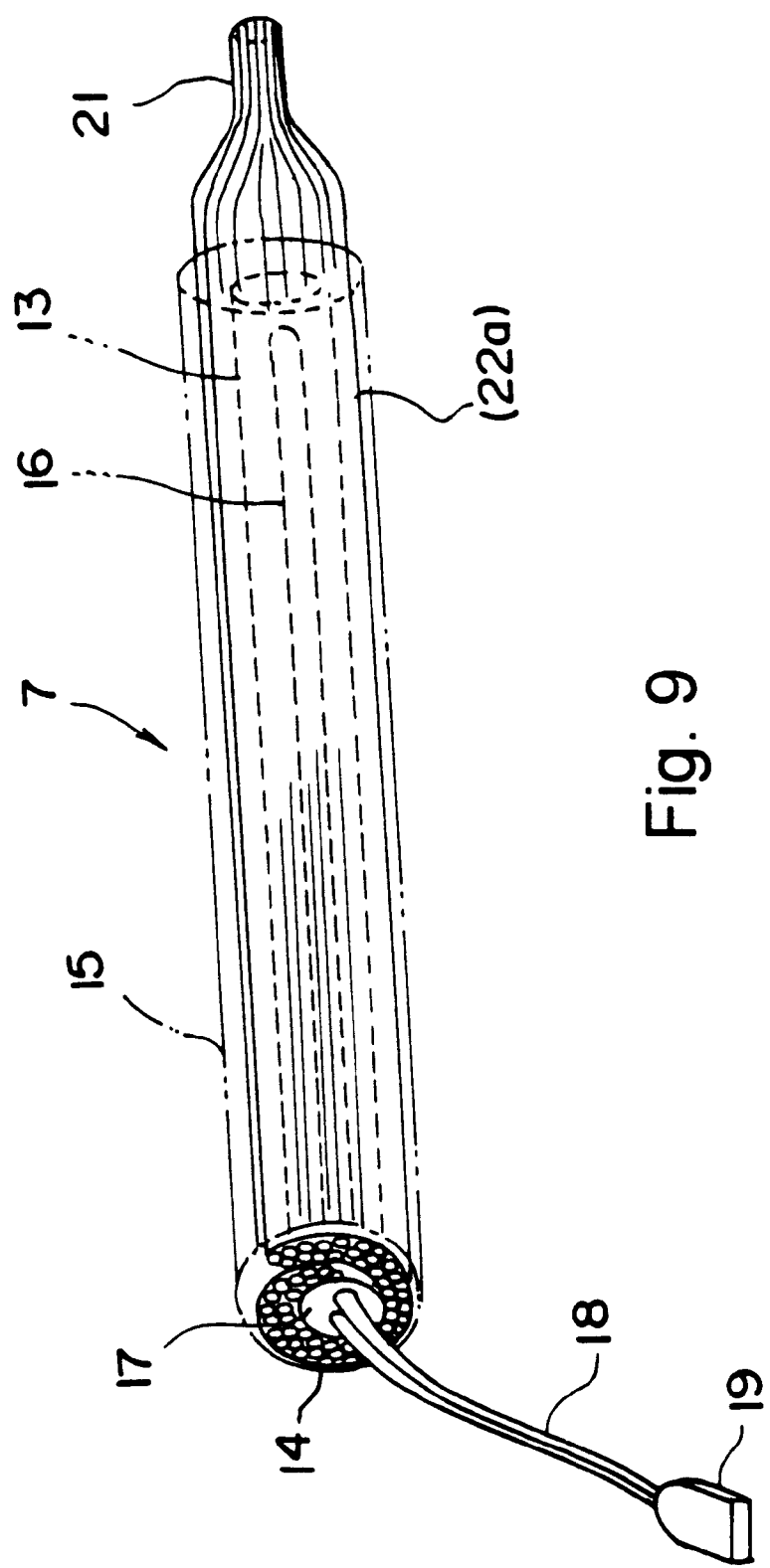
FIG. 9 is a perspective view showing a humidifying element according to a third embodiment of the present invention.

FIG. 9 shows a humidification unit according to a third embodiment of the present invention. In the third embodiment, multiple hollow fibers 14 are bundled (joined) on the side of exothermic member 13 opposite the electric current supply side of the exothermic member 13 and the bundled portion is formed with connector 21 to be connected to water bag 24. This arrangement allows connector 21 to be formed without taking an electric current supply system into consideration, thereby making the formation of connector 21 easier.

Of course, the present invention contemplates that connector 21 may be formed on the same side of exothermic member 13 to which electric current supply is connected.

Figure 10:
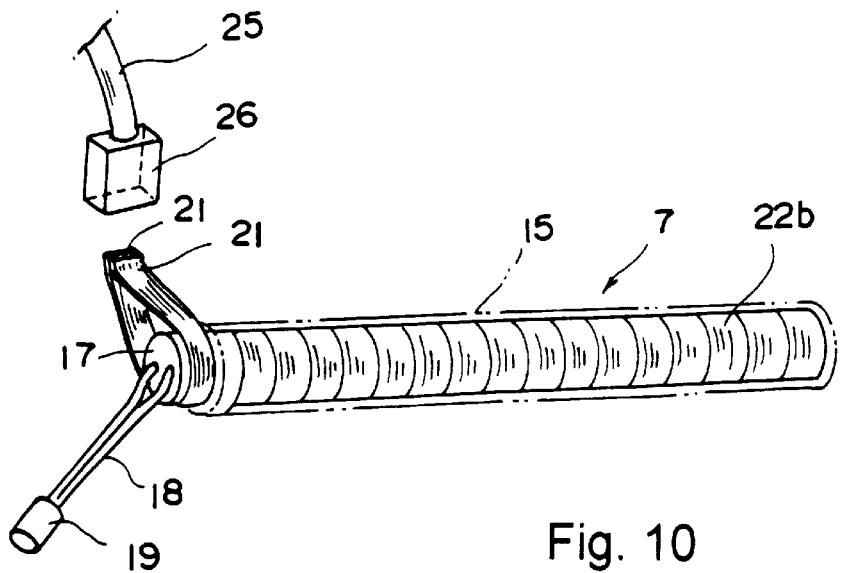
FIG. 10 is a perspective view showing a humidifying element according to a fourth embodiment of the present invention.
Figure 11:
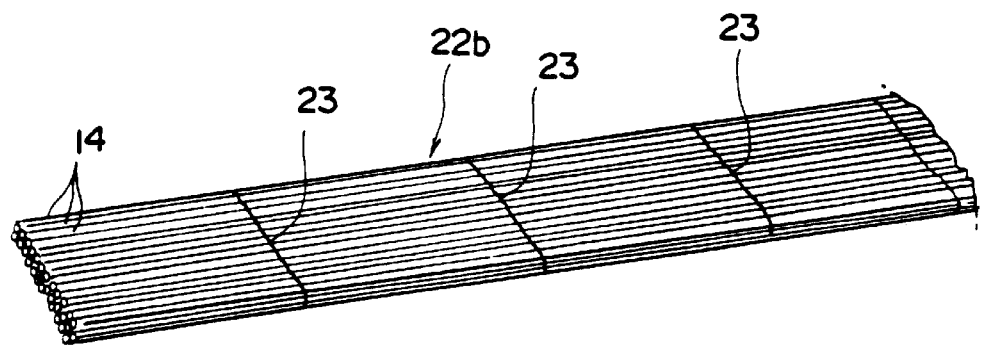
FIG. 11 is a perspective view showing the multiple hollow fibers arranged in a strip according to the fourth embodiment of the present invention.
Figure 12:
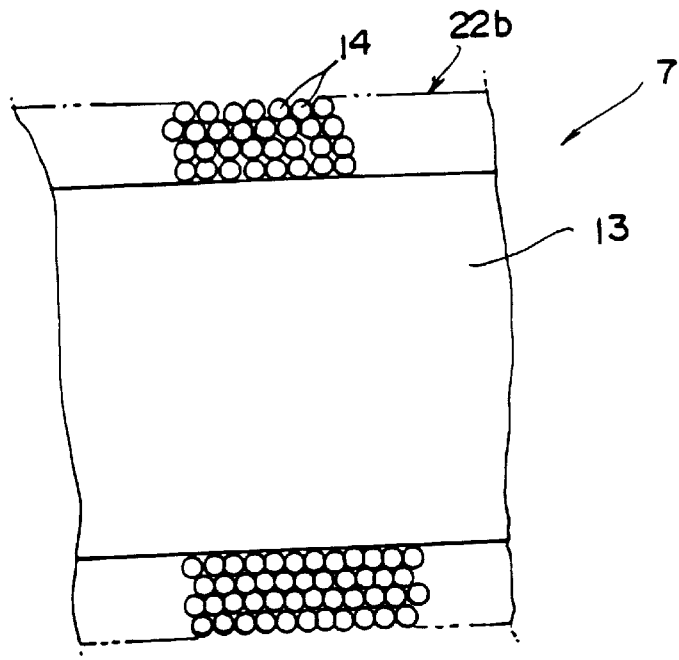
FIG. 12 is a cross-sectional view showing the multiple hollow fibers wound around the exothermic member.

FIGS. 10–12 show a humidification unit according to a fourth embodiment of the present invention. In the fourth embodiment, minute openings are provided in multiple hollow fibers 14, each opening being large enough to allow water vapor to permeate therethrough, yet small enough to fail to permeate water therethrough. The multiple hollow fibers are formed into a strip 22b by connecting each of multiple hollow fibers 14 integrally to each other with a string member 23 or the like as shown. Multiple hollow fiber strip 22b is then wound around exothermic member 13 in a spiral manner, and humidifying element 7 is then prepared by inserting multiple hollow fiber strip 22b and exothermic member 13 into extendable mesh cover tube 15 in a tightly engaged manner.

In the preparation of the humidifying element in the manner as described herein above, there can also be achieved the action and effects similar to those as achieved by the method for the preparation of the humidification unit in the first embodiment of the present invention.

In the fourth embodiment of the present invention, as shown in FIG. 10, the multiple hollow fiber strip 22b is wound around exothermic member 13, starting with a one end portion of the exothermic member, over the entire length thereof to the other end portion thereof and then continually turning from the other end portion thereof back to the one end portion thereof. Winding of multiple hollow fiber strip 22b around exothermic member 13 in this manner locates both end portions of multiple hollow fibers strip 22b at the one end portion of exothermic member 13 and both end portions of multiple hollow fibers strip 22b are formed with one connector 21. As a matter of course, at this time, both end portions of the multiple hollow fibers gathering 22b can be bundled together integrally and the bundled portion may be formed with one connector 21.

In the fourth embodiment of the present invention, the amount of multiple hollow fibers 14 held on exothermic member 13 can be increased, thereby improving the humidifying ability. At the same time, as both end portions of multiple hollow fiber strip 22b are located at one end portion of exothermic member 13, the humidification unit according to the fourth embodiment of the present invention can achieve the action and effects equivalent of those as achieved in the first embodiment (FIG. 3).

Figure 13:
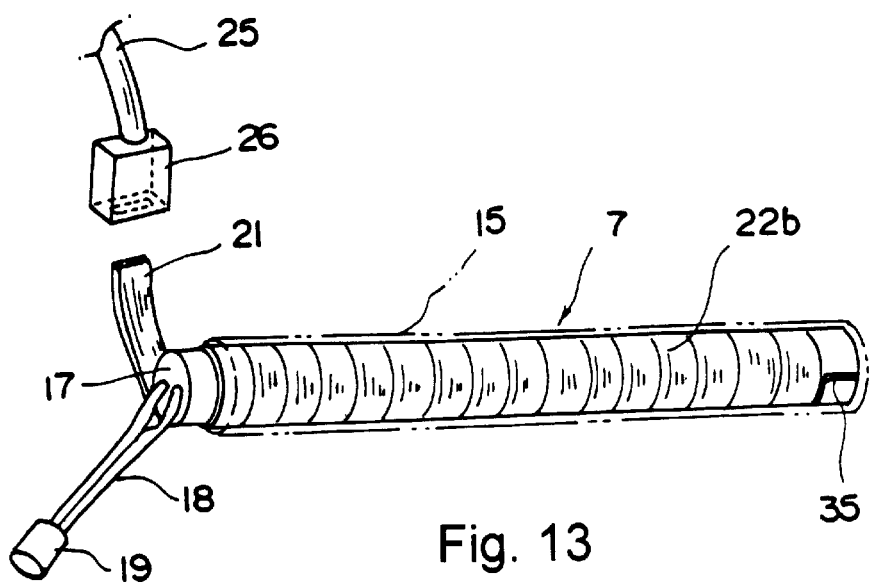
FIG. 13 is a perspective view showing a humidifying element according to a fifth embodiment of the present invention.

FIG. 13 shows a humidification unit according to a fifth embodiment of the present invention and specifically shows a variant of the manner of winding multiple hollow fiber strip 22b around exothermic member 13. In the fifth embodiment, multiple hollow fiber strip 22b is wound around exothermic member 13 starting with a one end portion of exothermic member 13 and extending over the entire length up to the other end portion of the exothermic member in a manner such that the one end portion of multiple hollow fiber strip 22b is located at the one end portion of the exothermic member and the other end portion of the multiple hollow fiber strip is located at the other end portion of the exothermic member. Further, the openings at end portion 35 of strip 22b are closed with adhesive agent or the like (the openings at end portion 35 of multiple hollow fiber strip 22b are closed is shown by oblique lines in the drawing). Furthermore, one end portion of multiple hollow fiber strip 22b is bundled (joined) and the bundled portion is formed with connector 21.

As multiple hollow fiber strip 22b is wound around the exothermic member 13 in a spiral form in the manner as described herein above, even where connector 21 is to be located at one side of exothermic member 13 that is the same and where the electric current supply is provided to exothermic member 13, connector 21 can be formed without taking the electric current supply system into consideration, thereby facilitating the preparation of connector 21.

Figure 14:
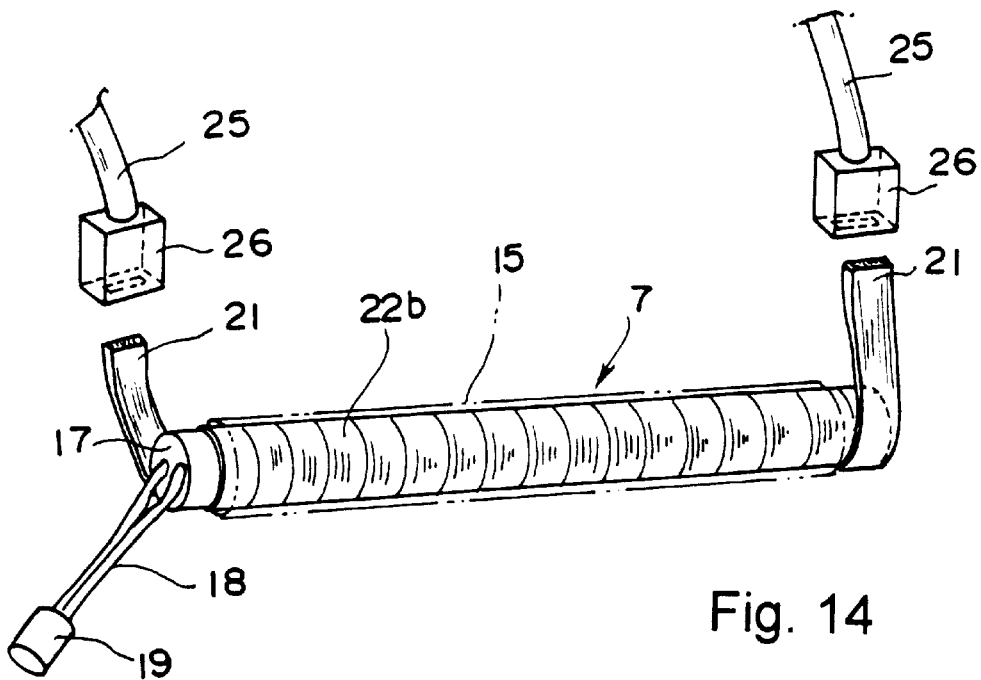
FIG. 14 is a perspective view showing the humidifying element according to a sixth embodiment of the present invention.

FIG. 14 shows a humidification unit in accordance with a sixth embodiment of the present invention, which is a variant of the fifth embodiment as described herein above. In the sixth embodiment, one end portion of multiple hollow fiber strip 22b, which is wound around exothermic member 13, is located at one end portion of the exothermic member 13, and the other end portion of strip 22b is located at the other end portion of the exothermic member 13. Further, multiple hollow fiber strip 22b is bundled (joined) at each end portion thereof, and each of the bundled portions is formed with a connector 21. This arrangement can achieve the action and effects equivalent of those as achieved by humidifying element 7 in the second embodiment.

Figure 15:
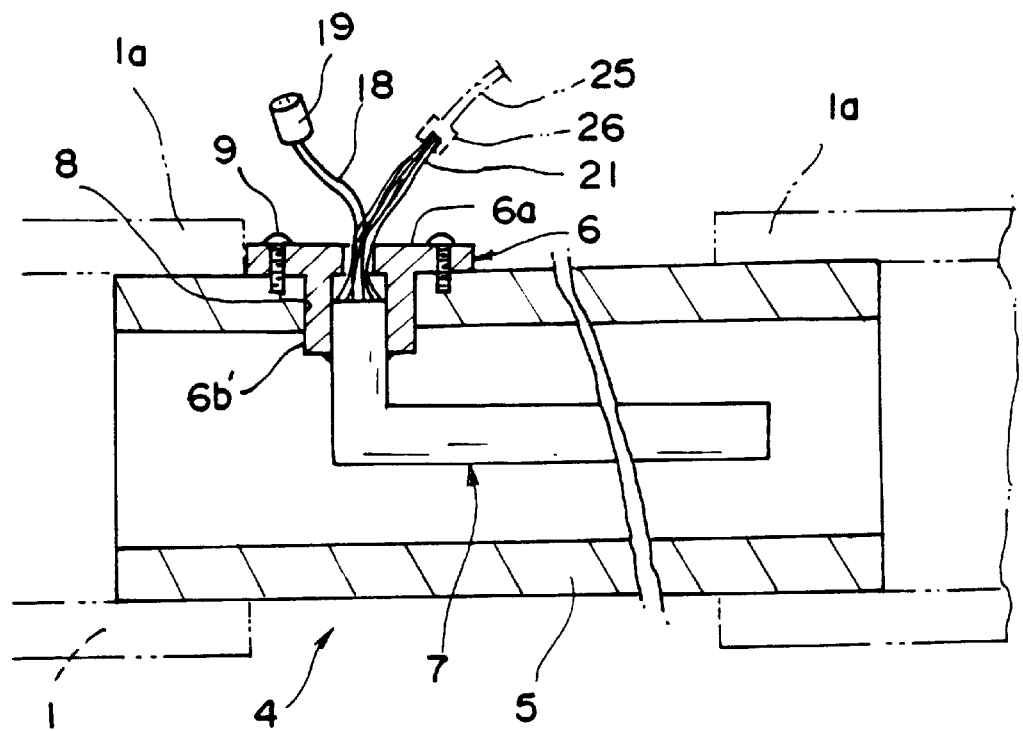
FIG. 15 is a perspective view showing the humidifying element according to a seventh embodiment of the present invention.

FIG. 15 shows a humidification unit in accordance with a seventh embodiment of the present invention, which is a variant of the humidification unit 4. In the humidification unit 4 of FIG. 15, mounting flange 6 is arranged in a manner such that holding portion 6b', is disposed standing upright from flange portion 6a and one end portion of humidifying element 7 is curved at a nearly right angle with respect to the other end portion thereof. Further, one end portion of humidifying element 7 is held to holding portion 6b' by engagement therewith.

In this case, humidifying element 7 can be disposed with the other end portion thereof extending in the axial direction of connection tube 5 by mounting mounting flange 6 on connection tube 5.

Figure 16:
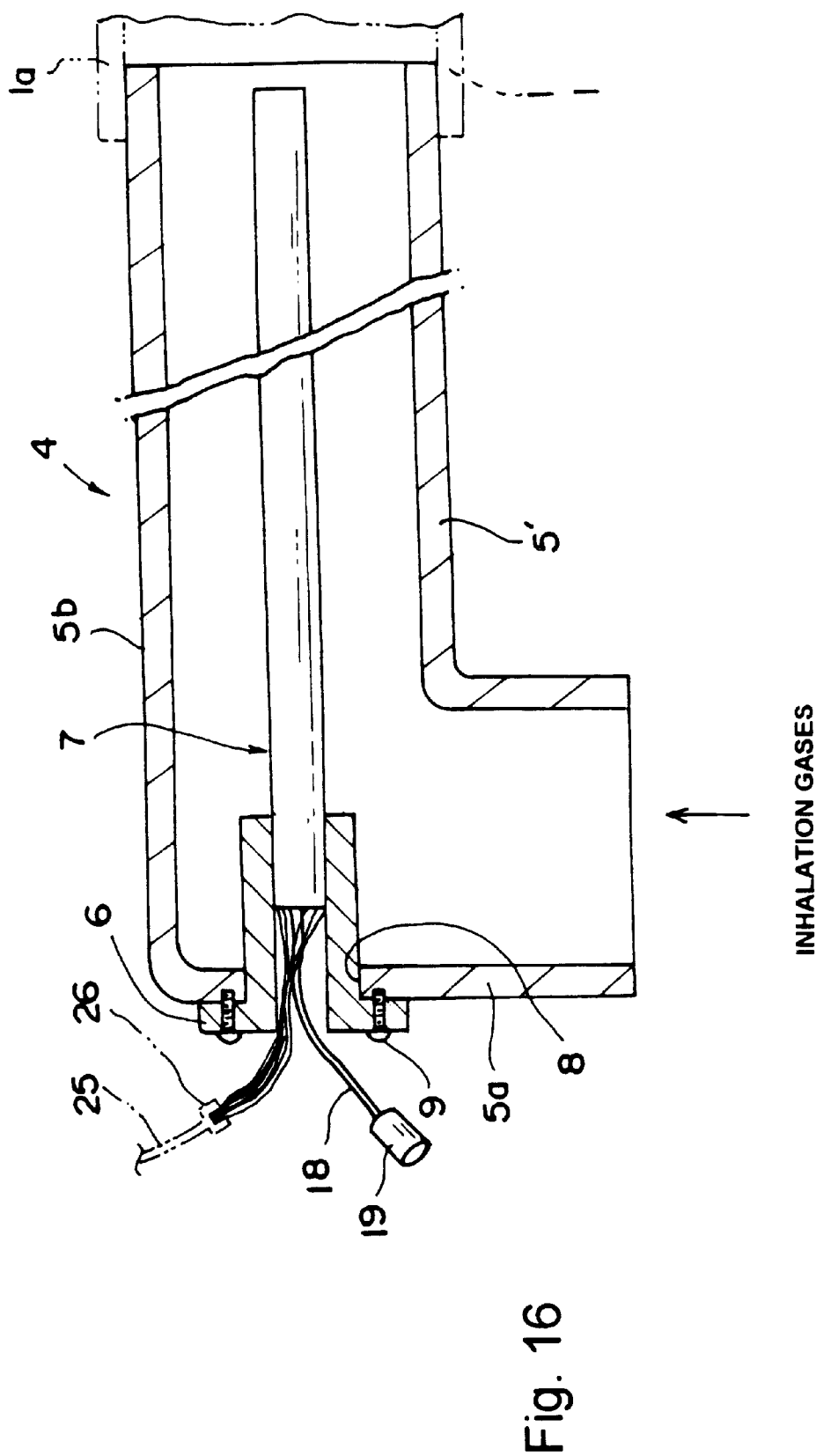
FIG. 16 is a perspective view showing the humidifying element according to an eighth embodiment of the present invention.

FIG. 16 shows a humidification unit in accordance with an eighth embodiment of the present invention. In the eighth embodiment, connection, tube 5' is a generally L-shaped tube and is disposed in such a manner that one end portion of humidifying element 7 is mounted through mounting flange 6 on a first tube portion 5a on one end of connection tube 5' in a region where the end portion of humidifying element 7 faces a sectional surface of the path defined in a second tube portion 5b on the other side of connection tube 5'. The other end of the humidifying element 7 extends in an axial direction of second tube portion 5b on the other side of connection tube 5' in second tube portion 5b.

This arrangement allows the generally L-shaped tube to be detachably mounted to patient circuit 1 in the same manner as in the first embodiment described above. In this embodiment, first tube portion 5a on one side of the generally L-shaped tube 5' can be employed as a supporting portion (a mounting portion) for supporting humidifying element 7 with high precision and further humidifying element 7 is set ready for use simply by inserting humidifying element 7 into mounting opening 8 of connection tube 5' at a right angle to the first tube portion 5a on one side of connection tube 5'.

Figure 17:
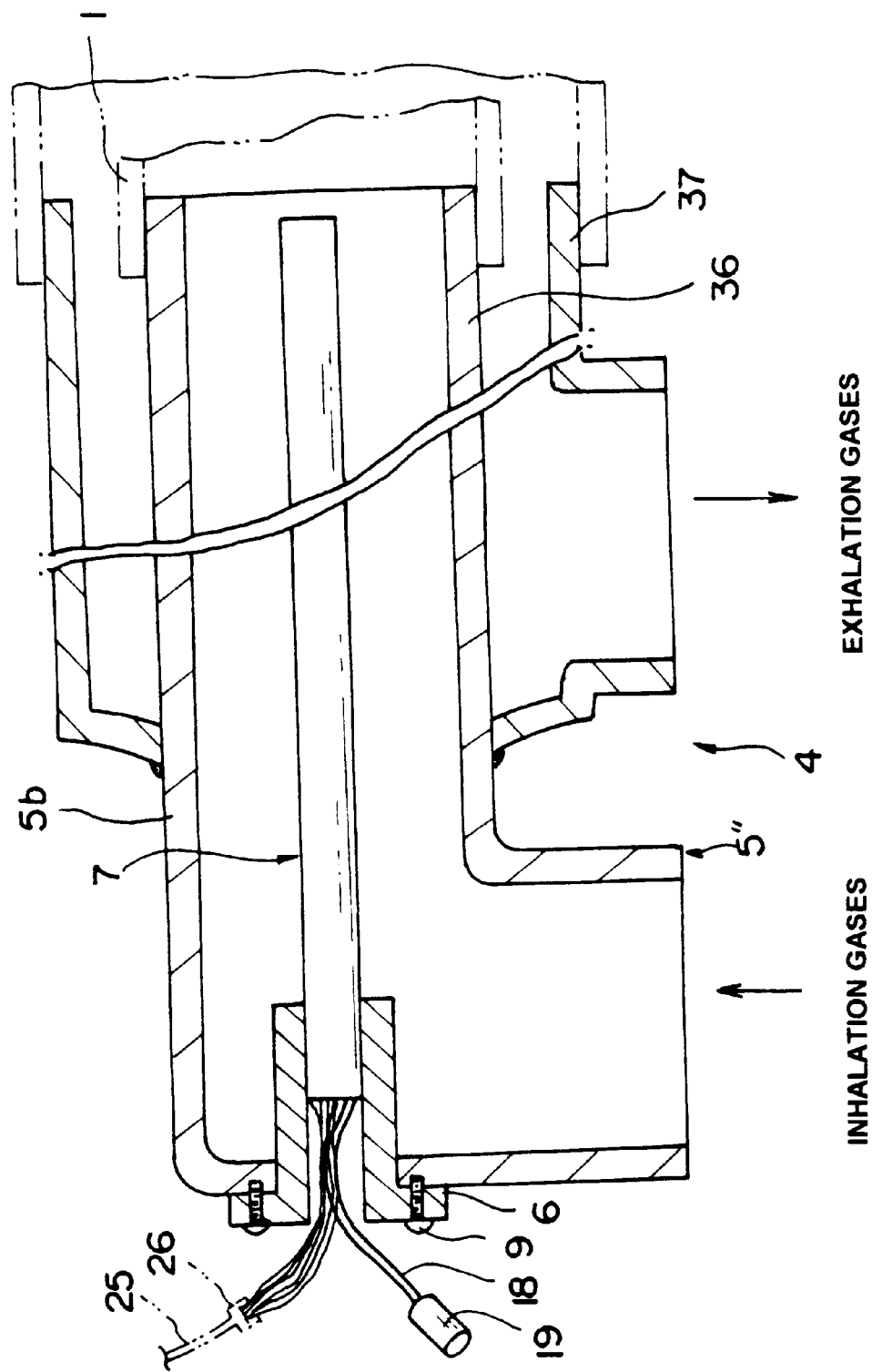
FIG. 17 is a perspective view showing the humidifying element according to a ninth embodiment of the present invention.

FIG. 17 shows a humidification unit according to a ninth embodiment of the present invention, which is a variant of the humidification unit according to the eighth embodiment as described herein above. In the ninth embodiment, connection tube 5" is of an inner-outer double tube structure. A second tube portion 5b on one side of connection tube 5" is used as done in the eighth embodiment and may be further employed as an inner tube 36 of the connection tube according to this embodiment. Inner tube 36 is disposed such that an outer tube 37 encloses the outer periphery of inner tube 36, thereby forming a ring-shaped path around and between an outer wall surface of the inner tube and an inner wall surface of the outer tube.

In this embodiment, connection tube 5" can be connected to an artificially respiratory circuit of an inner-outer double tube structure and the humidification unit according to this embodiment can be set readily to such an artificially respiratory circuit. In this case, exhaled gases are allowed to flow on the side of the outer tube (between the inner tube and the outer tube) and it is possible to prevent water vapors within the inner tube from condensing by using the heat from the exhaled gases flowing in the ring-shaped path.

FIG. 18 shows a humidification unit in a tenth embodiment of the present invention, which shows a variant of exothermic member 13. In the tenth embodiment, a heat pipe 38 is employed as the exothermic member and a heater 39 is mounted on a one end portion of heat pipe 38.

This arrangement of the exothermic member can simplify the structure of the humidification unit, because it is not necessary to ensure insulation in a region where multiple hollow fibers 14 are held and humidified. Further, using a general intensity member for heat pipe 38, the position of the multiple hollow fibers 14 held to the heat pipe can be enhanced to a higher extent. Further, by using heater 39 as a heat source of an endothermic portion of heat pipe 38, the action of the heat pipe 38 as the exothermic member 13 can be ensured.

Although the invention has been described in detail for the purpose of illustration based on what is currently considered to be the most practical and preferred embodiments, it is to be understood that such detail is solely for that purpose and that the invention is not limited to the disclosed embodiments, but, on the contrary, is intended to cover modifications and equivalent arrangements that are within the spirit and scope of the appended claims.

What is claimed is:

1. An artificial respiratory system comprising:
   (a) a pressure generator adapted to generate a flow of breathing gas;
   (b) a patient circuit coupled to the pressure generator so as to deliver the flow of breathing gas to the patient; and
   (c) a humidification unit disposed in the patient circuit, the humidification unit comprising:
      (1) an exothermic member having an outer surface, and
      (2) a plurality of hollow fibers disposed on the outer surface of the exothermic member, wherein each hollow fiber in the plurality of hollow fibers includes a fluid carrying channel defined by a peripheral wall of the hollow fiber for carrying fluid proximate to the outer surface of the exothermic member, wherein the peripheral wall of each hollow fiber has a plurality of minute openings that are large enough to allow a gas to pass therethrough yet small enough to prevent a liquid from passing therethrough so that fluid carried in the channel of each hollow fiber does not contact the exothermic member.

2. The artificial respiratory system of claim 1, wherein the exothermic member includes a heating wire adapted to generate heat responsive to an electrical current being provided to the heating wire.

3. The artificial respiratory system of claim 1, further comprising a fluid connector provided at a first end of the plurality of hollow fibers to communicate a liquid to fluid carrying channel of each of the plurality of hollow fibers, and wherein a second end of the plurality of hollow fibers is closed.

4. The artificial respiratory system of claim 1, wherein the exothermic member and the plurality of hollow fibers define a humidification element, and further comprising a support member coupled to the humidification element and removeably to the patient circuit.

5. The artificial respiratory system of claim 1, further comprising a fluid delivery system coupled to the plurality of hollow fibers so as to deliver a fluid thereto.

6. The artificial respiratory system of claim 5, wherein the fluid delivery system includes:
   a fluid source;
   a fluid communication conduit coupled to the fluid source and the plurality of hollow fibers;
   a fluid flow monitor associated with the fluid communication conduit for monitoring a flow of fluid therethrough; and
   an alarm system associated with the flow monitor that provides an alarm responsive to the flow of fluid in the fluid communication conduit falling outside a predetermined threshold.

7. The artificial respiratory system of claim 5, wherein the fluid delivery system includes:
   a fluid source;
   a fluid communication conduit coupled to the fluid source and the plurality of hollow fibers; and
   a fluid control system associated with the fluid source or the fluid communication conduit for controlling a flow of the fluid from to the plurality of hollow fibers.

8. The artificial respiratory system of claim 1, further comprising:
   a power source;
   an electrical connector coupled to the power source and the exothermic member for supplying electrical power from the power source to the exothermic member.

9. The artificial respiratory system of claim 8, further comprising a power control system associated with the power source or the electrical connector for controlling the power provided to the exothermic member.

10. The artificial respiratory system of claim 1, further comprising a sensor disposed in the patient circuit and adapted to monitor a characteristic of the flow of breathing gas carried by the patient circuit.

11. The artificial respiratory system of claim 10, further comprising an alarm system associated with the sensor that provides an alarm responsive to a parameter monitored by the sensor falling outside a predetermined threshold.

12. A method of providing artificial respiration comprising:
   (a) generating a flow of breathing gas;
   (b) communicating the flow of breathing gas to the patient via a patient circuit;
   (c) providing a humidification unit in the patient circuit, wherein the humidification unit comprises:
      (1) an exothermic member having an outer surface, and
      (2) a plurality of hollow fibers disposed on the outer surface of the exothermic member, wherein each hollow fiber in the plurality of hollow fibers includes a fluid carrying channel defined by a peripheral wall of the hollow fiber for carrying fluid proximate to the outer surface of the exothermic member, wherein the peripheral wall of each hollow fiber has a plurality of minute openings that are large enough to allow a gas to pass therethrough yet small enough to prevent a liquid from passing therethrough so that fluid carried in the channel of each hollow fiber does not contact the exothermic member;

(d) delivering a flow of fluid to the plurality of hollow fibers; and (e) heating the fluid in plurality of hollow fibers via the exothermic member.

13. The method of claim 12, wherein the exothermic member includes a heating wire, and wherein heating the fluid comprises providing electrical energy to the exothermic member to heat the fluid in the plurality of hollow fibers.

14. The method of claim 12, further comprising:

monitoring a flow of fluid delivered to the plurality of hollow fibers; and actuating an alarm responsive to the monitored flow falling outside a predetermined threshold.

15. The method of claim 12, further comprising:

monitoring a characteristic of the flow of breathing gas; and actuating an alarm responsive to the monitored characteristic falling outside a predetermined threshold.

* * * * *